(12) United States Patent
Anderson et al.

(10) Patent No.: US 8,781,851 B2
(45) Date of Patent: Jul. 15, 2014

(54) DYNAMIC CLAIMS ADJUDICATION

(75) Inventors: Lori L. Anderson, Solana Beach, CA (US); Mai Ly Thi Hoang, Irving, TX (US); Chi Shing Chan, San Diego, CA (US); Jose Eli J. Golez, Jr., Oceanside, CA (US)

(73) Assignee: Medimpact Healthcare Systems, Inc., San Diego, CA (US)

( * ) Notice: Subject to any disclaimer, the term of this patent is extended or adjusted under 35 U.S.C. 154(b) by 784 days.

(21) Appl. No.: 12/913,685

(22) Filed: Oct. 27, 2010

(65) Prior Publication Data

US 2012/0109839 A1    May 3, 2012

(51) Int. Cl.
*G06Q 50/00* (2012.01)
*G06Q 10/00* (2012.01)

(52) U.S. Cl.
USPC .................................................... 705/2

(58) Field of Classification Search
CPC ............. G06Q 30/206–30/207; G06Q 30/236; G06F 19/322; G06F 19/324–19/328; G06F 19/3462; G06F 19/3456
USPC ........................................... 705/2–3
See application file for complete search history.

(56) References Cited

U.S. PATENT DOCUMENTS

| | | | |
|---|---|---|---|
| 5,930,759 A | 7/1999 | Moore et al. | |
| 6,735,569 B1 | 5/2004 | Wizig | |
| 7,490,047 B2 | 2/2009 | Brown et al. | |
| 7,734,483 B1 | 6/2010 | Smith | |
| 7,769,606 B2 | 8/2010 | Boone et al. | |
| 2001/0037216 A1* | 11/2001 | Oscar et al. ...................... 705/2 |
| 2002/0049617 A1 | 4/2002 | Lencki et al. | |
| 2002/0111832 A1 | 8/2002 | Judge | |
| 2004/0006490 A1 | 1/2004 | Gingrich et al. | |
| 2004/0117323 A1 | 6/2004 | Mindala | |
| 2005/0055251 A1 | 3/2005 | Ashley et al. | |
| 2006/0149416 A1* | 7/2006 | Mohapatra et al. ........... 700/242 |
| 2006/0184391 A1* | 8/2006 | Barre et al. ...................... 705/2 |
| 2006/0212345 A1 | 9/2006 | Soza et al. | |
| 2007/0276697 A1 | 11/2007 | Wiley, II et al. | |
| 2008/0059242 A1 | 3/2008 | Stanford | |
| 2008/0312956 A1 | 12/2008 | Momita et al. | |
| 2009/0006141 A1 | 1/2009 | Karr | |
| 2009/0265189 A1 | 10/2009 | Bartholomew, III et al. |
| 2009/0276249 A1 | 11/2009 | Dust et al. | |
| 2010/0094766 A1 | 4/2010 | Li et al. | |
| 2010/0161351 A1 | 6/2010 | Howe et al. | |

OTHER PUBLICATIONS

Alderman, Lesley; "Not All Drugs are the Same After All"; New York Times; Published: Dec. 18, 2009; Access Jun. 13, 2013; http://www.nytimes.com/2009/12/19/health/19patient.html?pagewanted=1&_r=3&ref=health&.*

* cited by examiner

*Primary Examiner* — Minnah Seoh
(74) *Attorney, Agent, or Firm* — Pattric J. Rawlins; Procopio, Cory, Hargreaves & Savitch LLP (57) ABSTRACT

A dynamic claims adjudication system is provided that implements a dynamic claims adjudication process to provide flexible determination of the adjudication rule set to be used to adjudicate a claim for a particular prescription drug regardless of the mandates of the formulary and the rigidity of the tier into which the drug is placed on the formulary. The claims adjudication system and corresponding methods dynamically determine the adjudication rule set to be used to adjudicate a claim based on an analysis of criteria and identification of a tier changing criteria. Accordingly, the rigidity of conventional formulary based claims adjudication is eliminated in favor of dynamic and flexible real time claims adjudication.

20 Claims, 2 Drawing Sheets

DYNAMIC CLAIMS ADJUDICATION

BACKGROUND

1. Field of the Invention

The present invention relates generally to prescription drug benefits programs and more specifically relates to an improved dynamic claims adjudication system for adjudicating consumer purchases that are covered by such programs.

2. Related Art

Conventional systems for electronic claims adjudication by pharmacy benefits management ("PBM") companies have been around for some time. A PBM is an administrator of prescription drug programs. PBMs are primarily responsible for adjudication and paying claims for covered prescription drugs that are purchased by consumers who are members of the prescription drug benefit program. Other typical PBM services include developing and maintaining the drug formulary (the list of drugs covered by the prescription drug benefits program and their associated tiers), contracting with pharmacies, and negotiating discounts and rebates with drug manufacturers. Conventional PBM claim adjudication systems are typically employed when a member attempts to purchase a drug and the drug purchase is to be wholly or partially covered by a prescription drug benefits program. A prescription drug benefits program may be provided to the member through an employer health plan (e.g., ERISA plans, self insured plans, managed care plans, Taft-Hartley trust plans, etc.), or a privately purchased health plan, a government sponsored plan (e.g., Medicare, Medicaid or any other city, state or local or federal government plan) or directly from a PBM provider. In such a transaction, the originating entity (e.g., a pharmacy) electronically transmits a claim to the PBM through a switch company for adjudication of the claim. The PBM adjudicates the claim to validate, among other things, that the member has a valid prescription drug benefits program, that the prescribing doctor is valid, and that the drug is covered by the prescription drug benefits program. The PBM sends an electronic response back to the pharmacy that denies the transaction or approves the transaction and also identifies the co-pay amount.

At a high level, the overall process of adjudicating drug purchase claims covered by the variety of prescription drug benefits programs offered under various types of health care plans is similar such that the pharmacy electronically transmits a claim to the PBM, the claim is adjudicated, and an electronic response is sent back to the pharmacy. However, one of the significant challenges faced by PBMs during claim adjudication is that certain claims need to be adjudicated differently. For example, claims that are covered by a prescription drug benefits program provided under a Medicare Part D plan are adjudicated differently than claims that are covered by a prescription drug benefits program provided by a privately purchased health plan.

One significant drawback of conventional adjudication of prescription drug purchase claims is that they adjudicate claims in real time based on the formulary, which imposes rigid drug classifications that, for all members and all transactions, define the universe of available drugs and their associated tiers. The formulary also dictates the copays of the various drugs that are available and the respective adjudication rule set to be used to adjudicate a claim for a particular drug on a particular tier. Therefore, what is needed is a system and method that overcomes these significant problems found in the conventional systems as described above.

SUMMARY

Accordingly, the dynamic claims adjudication systems and methods described herein are directed toward a dynamic claims adjudication process that provides for flexible determination of adjudication rule sets to be used to adjudicate a claim for a particular drug regardless of the mandates of the formulary and the rigidity of the tier into which the drug is placed on the formulary. The claims adjudication system and corresponding methods described herein dynamically determine the adjudication rule set to be used to adjudicate a claim based on an analysis of certain member specific criteria. Accordingly, the rigidity of conventional formulary based claims adjudication is ameliorated in favor of dynamic and flexible real time claims adjudication.

More specifically, when a claim is received from a pharmacy, member specific criteria are analyzed to determine the adjudication rule set to employ when adjudicating the claim for validation. Furthermore, during application of the dynamically determined adjudication rule set to the claim, the member copay is determined. Accordingly, individual members having identical prescription drug benefits program coverage may be assigned different copays based on each individual member's specific criteria. Similarly, a single individual member may be assigned a different copay for identical (e.g., same drug, same insurance coverage, same formulary) first and second transactions that occur at different times because the individual member's specific criteria has changed between the two transactions.

Advantageously, the dynamic claims adjudication systems and methods described herein allow dynamically switching tiers based on a variety of factors including, for example, step therapy. Step therapy is a series of therapies or other events related to treatment, for example, taking a prescribed drug or visiting a counselor could be treatment related events according to a particular step therapy. In a step therapy example, the patient specific criteria would include information about the patient's prior treatment and whether the member had completed certain required therapies. If the member had completed the required therapies, then the tier level for adjudicating the current claim may be changed in order to allow purchase of a certain previously disallowed drug or to allow a reduced copay. Thus, if the patient had already taken the generic drug for treatment and then had taken the less expensive brand name drug for treatment, then the current claim for the most expensive drug available would be adjudicated at the lowest tier copayment rate so that the member copay amount is the same as it was for the generic.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments as disclosed herein provide systems and methods for real time claims adjudication that dynamically determines the rule set to be used for adjudicating the claim based on an analysis of member specific criteria. For example, one method as disclosed herein allows for the claim adjudication instructions used to adjudicate a prescription drug purchase claim to be dynamically determined in real time based on member specific criteria that alters the tier level at which the drug to be purchased is adjudicated.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
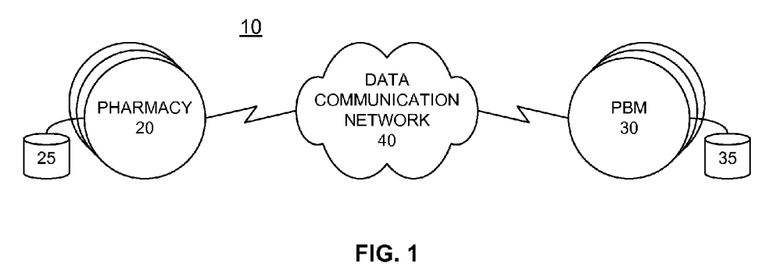
FIG. 1 is a network diagram illustrating an example system for dynamic claims adjudication according to an embodiment of the invention.

FIG. 1 is a network diagram illustrating an example system 10 for dynamic claims adjudication according to an embodiment of the invention. In the illustrated embodiment, the system 10 comprises a pharmacy 20 that is communicatively coupled with PBM 30 via a data communication network 40. The system 10 may include more than one pharmacy 20 and more than one PBM 30.

The pharmacy 20 can be a brick and mortar store, an online ecommerce website or application, or any other sort of entity, system or device that is capable of handling a member prescription drug purchase transaction. The pharmacy 20 may include one or more processor enabled communication devices (not shown) that are capable of communicating with the PBM 30 over the network 40 and storing data in and retrieving data from the data storage area 25. The data storage area 25 may include any form of memory including volatile and non-volatile. In one embodiment, the data storage area 25 includes non-transitory computer readable media. Example architectures that can be employed for such communication devices are described later with respect to FIG. 5.

Similarly, the PBM 30 may include one or more processor enabled communication devices (not shown) that are capable of communicating with the pharmacy 20 over the network 40 and storing data in and retrieving data from the data storage area 35. The data storage area 35 may include any form of memory including volatile and non-volatile. In one embodiment, the data storage area 35 includes non-transitory computer readable media. Example architectures that can be employed for such communication devices are described later with respect to FIG. 5.

The network 40 may include a variety of communication infrastructure including direct wired connections, personal area networks, local area networks, wide area networks, metropolitan area networks and any other communication infrastructure including telephone networks and the Internet. The network 40 may be wired or wireless or a combination of wired and wireless and may also be capable of transmitting voice or data traffic or a combination of voice and data traffic. The network 40 may also be public or private or a combination of public and private and may transmit information using a variety of protocols, as will be understood by those skilled in the art.

In one embodiment, the data communication network 40 includes a switch (not shown) that operates in the communication infrastructure between the pharmacy 20 and the PBM 30 and serves to electronically route prescription drug purchase claims to the appropriate PBM 30 based on member provided information (e.g., a prescription drug benefits program card or other eligibility data or evidence of coverage).

In operation of the system 10, a member of a prescription drug benefits program attempts to purchase a prescribed drug at the pharmacy 20. The pharmacy 20 collects certain information from the member to validate the prescription drug purchase transaction (also referred to herein as a "claim"). For example, this information may be obtained from the member's health plan card. The pharmacy 20 sends an electronic claim adjudication request to the PBM 30 via the network 40. The claim adjudication request seeks approval of the drug purchase transaction from the PBM 30. The PBM 30 adjudicates the claim adjudication request to validate or determine various elements of the claim. For example, such elements of the claim may include member enrollment status, inclusion of the drug on the formulary and amount of member copay.

During claim adjudication, the PBM 30 analyzes information relevant to the particular claim being adjudicated. During the analysis, the PBM 30 determines the original tier for the claim. The tier for a claim determines at least a portion of the claim adjudication instructions that are carried out by PBM 30 to adjudicate the claim. During the analysis, the PBM 30 additionally identifies any tier changing criteria. Tier changing criteria may be identified based on prior drug purchases (e.g., historical claim adjudication data), doctor visits (e.g., annual physical, colonoscopy, etc.), successful or unsuccessful performance of desired steps (e.g., step therapies, time sensitive events), lab data values (e.g., lab test results, white blood cell count, iron levels, etc.), patient diagnosis (e.g., diabetes, cancer, asthma, hemophiliac, allergies, etc.), and pharmacogenomics (e.g., optimization of drugs and drug combinations to be patient specific). Other tier changing criteria will become apparent to those skilled the art and are all intended to be covered by the scope of the present description. If one or more tier changing criteria are identified, such tier changing criteria are analyzed by the PBM 30 to determine the end tier. The end tier is the tier that will be used by the PBM 30 to determine at least a portion of the claim adjudication instructions for the current claim.

As the claim adjudication process continues, the PBM 30 carries out the claim adjudication instructions in accordance with the end tier and upon completion of the claim adjudication process the PBM 30 provides the results of the claim adjudication to the pharmacy 20 in response to the claim adjudication request.

Figure 2:
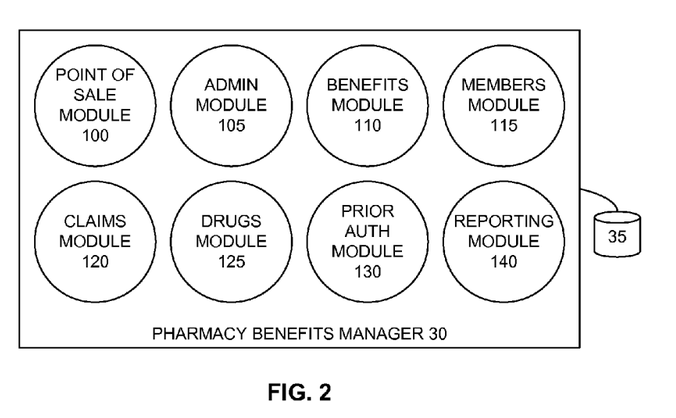
FIG. 2 is a block diagram illustrating an example PBM according to an embodiment of the invention.

FIG. 2 is a block diagram illustrating an example PBM 30 according to an embodiment of the invention. In the illustrated embodiment, the PBM 30 comprises a point of sale ("POS") module 100, an administrative module 105, a benefits module 110, a members module 115, a claims module 120, a drugs module 125, a prior authorizations module 130, and a reporting module 135. As previously discussed, the PBM 30 includes a processor enabled communication device and this device is capable of accessing information and the various modules of the PBM 30 stored in data storage area 35 and executing those modules using the processor. Additionally, Each of the various modules of the PBM 30 are configured to store and manage information in the data storage area 35 that is related to each module's respective operation and communication with other modules of the PBM 30 or external modules and/or devices.

Point of sale ("POS") module 100 is configured to receive a claim adjudication request, adjudicate the claim, and provide claim adjudication results in response to the claim adjudication request. The POS module 100 receives a claim adjudication request from a pharmacy (not shown) via a communication link. The PBM 30 may include other modules (not shown) that manage the communication link and its corresponding physical media (e.g., wired or wireless networks, direct cable connections, modems, etc.). Similarly, the POS module 100 provides the claim adjudication results to a pharmacy (not shown) via a communication link that may be managed by other modules (not shown) stored in memory 35 of the PBM 30. In one embodiment, there is a switch operating in the communication infrastructure between the pharmacy and the PBM 30 and in such an embodiment, the POS module 100 receives the claim adjudication request indirectly from pharmacy through the switch and provides the claim adjudication results to the pharmacy indirectly through the switch.

During claim adjudication, the POS module 100 communicates with a variety of other modules on the PBM 30 and accesses information and data stored in the data storage area 35 in order to adjudicate the claim. For example, the POS module 100 may communicate with the benefits module 110 to obtain information regarding the prescription drug benefits program and related claim adjudication instructions. Additionally, the POS module 100 may communicate with the members module 115 to obtain information about the member associated with the claim adjudication request. Member information may include demographic data about the member as well as certain details about the member's particular levels and/or types of coverage under the prescription drug benefit program. The POS module 100 may also communicate with the claims module 120 to obtain historical claim information for a particular member or other historical claim information that is related to the claim adjudication request. For example, during the claim adjudication process, the POS module 100 may request from the claims module 120 information related all historical claims within the last 120 days for the member associated with the current claim adjudication request. Alternatively, the POS module 100 may request from the claims module 120 information related to historical claims involving the particular drug, pharmacy, prescribing physician, prescription drug benefits program, or any combination of these and other claim related information stored in data storage area 35.

The POS module 100 may also communicate with the drugs module 125 to obtain information related to the drug or drugs associated with the claim adjudication request. For example, the drugs module 125 may maintain in data storage area 35 the national drug code ("NDC") listing of prescription drugs and their corresponding therapeutic classes and prices. In claim adjudication, this information can be used by the POS module 120 to confirm that the requested drug is approved for purchase and also to determine the member price to be paid, for example when the tier level of the drug suggests that the member copay is a percentage of the price of the drug, e.g., with co-insurance or otherwise. The POS module 100 may also communicate with the prior authorization module 130 to identify any manual overrides that have been stored into data storage area 35. In conventional claim adjudication systems, prior authorizations constitute overrides during claim adjudication that mandate desired claim adjudication outcomes that are different from the natural result of the claim adjudication process based upon the unedited executed claim adjudication instructions. Accordingly, the POS module 100 may analyze the claim adjudication request and identify and carry out the claim adjudication instructions and then pursuant to a prior authorization edit provided by the prior authorization module 130, determine that the result of claim adjudication is other than the natural result of the claim adjudication instructions. In such a case, the claim adjudication process provides the pharmacy with a claim adjudication result that adheres to the result mandated by the prior authorization override rather than the claim adjudication result that was the natural consequence of carrying out the claim adjudication instructions. For example, if the natural result of the POS 100 claim adjudication is that the member has a copay of $15 to purchase the prescribed drug, a prior authorization based on financial hardship for the member might override the copay so that the claim adjudication result provided to the pharmacy indicates that the member copay is $0.

The POS module 100 may also communicate with the reporting module 140 to provide the reporting module with information related to claim adjudication results that can be incorporated by the reporting module 140 into informational reports directed to the PBM 30, the prescription drug benefits program administrator, the pharmacy, or even the member. Advantageously, the reporting module 140 is configured to access information stored in data storage 35 and is also configured to communicate with the various modules of PBM 30 in order to provide data and feature-rich reports to the various stakeholders that are involved in the implementation of a prescription drug benefits program. In one embodiment, the reporting module is configured to provide information including the original tier for an adjudicated claim, the end tier for the adjudicated claim and the corresponding reason for changing the tier from the original tier to the end tier.

The administrative module 105 is configured to receive characteristics, details and any other information related to the prescription drug benefits program and store that information in data storage area 35. Admin module 105 is also configured to manage the operational characteristics of the benefits module 110 so that the benefits module 110 is tailored to implement the prescription drug benefits program according to the policies established by the program administrator. For example, the prescription drug benefits program may include a formulary that defines a plurality of tiers into which the approved prescription drugs are assigned. In one embodiment, there are three tiers—a first tier for generic drugs, a second tier for single source drugs, and a third tier for multi-source drugs. In alternative embodiments, there may be more or fewer tiers into which the approved prescriptions drugs are assigned.

The benefits module 110 is configured to implement the prescription drug benefits program designed by a program administrator and communicates with the various other modules of PBM 30 to do so. The benefits module 110 is also configured to set up the rules, criteria and store data and instructions in the data storage area 35 that are used by the POS module 100 when adjudicating claims. For example, the benefits module 110 maintains information related to claim adjudication including member copay amounts, annual limits on payments, restrictions, desired therapies such as sequential steps, and previously approved prescription drug purchases. Advantageously, benefits module 110 allows a program administrator to design sequential therapies (also referred to as step therapies) such that dynamic claim adjudication provides members with economic incentives to adhere to the step therapy. For example, a member is prescribed a drug in a therapeutic class where a generic product, a single-source product, and a multi-source product are available with relative increasing cost for the different products. For the sake of the example, the cost of the generic product is $100, the cost of the single-source product is $200 and the cost of the multi-source product is $300. As previously, explained, the cost information may be obtained from the drugs module 125. The benefits module may also be configured to directly obtain the cost information from the data storage area 35. Furthermore, in this example because the different products are in the same therapeutic class, the member has the option of purchasing any of the three different products. Advantageously, the benefits module 110 is configured to provide claim adjudication instructions to the POS module 100 for the first drug purchase by the member that causes the purchase of the generic product to be a tier 1 purchase that has an associated member copay of $0, causes the purchase of the single-source product to be a tier 4 purchase that has an associated member copay of 50% (which results in a $100 copay in this example), and causes the purchase of the multi-source product to be a tier 5 purchase that has an associated member copay of 100% (which results in a $300 copay in this example). Accordingly, the member is economically motivated to purchase the generic product when first filling the prescription but the member also has the ability to purchase the single-source product or the multi-source product for a higher copay. In this case, the member purchases the generic product for $0 copay and the member's claim history stored in data storage area 35 reflects the purchase of the generic product.

Subsequently, the member receives a second prescription for the same therapeutic class of drug. Again, the member has the option of purchasing any of the three different prescription drug products. Advantageously, the benefits module 110 is configured to identify the purchase of the generic product in the member's claim history as a tier changing criteria and provide claim adjudication instructions to the POS module 100 for the second product purchase by the member that causes the purchase of the generic product to be a tier 1 purchase that has an associated member copay of $0, causes the purchase of the single-source product to be an improved tier purchase (e.g., also be a tier 1 purchase that has an associated member copay of $0), and again causes the purchase of the multi-source product to be a tier 5 purchase that has an associated member copay of 100% (which results in a $300 copay in this example). Accordingly, the improved tier for the purchase of the single-source product rewards the member for the initial purchase of the lower cost generic product, which is part of the desired step therapy according to the prescription drug benefits program, and now the member is economically motivated to continue to adhere to the desired step therapy by being able to obtain the single-source product for an improved, perhaps even $0 copay. If the member needs a third prescription for the same therapeutic class of drug, the benefits module 110 may be configured to provide claim adjudication instructions to the POS module 100 such that the multi-source product can also be purchased at an improved tier (i.e., a tier with a lower copay). In one embodiment, for this third purchase each of the three drug products may be a tier 1 purchase that has an associated member copay of $0. In an alternative embodiment, the three drug products may be purchased at tiers 1, 2 and 3, respectively. Advantageously, the system provides flexibility to the program administrator to design member incentives into the program.

The benefits module 110 is also configured to provide claim adjudication instructions to the POS module 100 for favorable dynamic claims adjudication based on a variety of other information that may be obtained from the data storage area 35 and/or from other modules of the PBM 30. In one embodiment, the benefits module 100 may identify seemingly unrelated member behaviors as tier changing criteria. For example, the presence in data storage area 35 of a health care professional's confirmation that the member has stopped smoking may be identified by the benefits module 110 as a tier changing criteria for the purchase of insulin. This capability of the benefits module 110 advantageously allows a prescription drug benefits program administrator to economically motivate a member to stop smoking if the program administrator believes that insulin is a more effective therapy for non-smokers. Conversely, the benefits module 110 also allows the program administrator to attempt to deter certain risky behavior in the same fashion. It should be understood that a tier changing criteria identified by the benefits module 110 may result in the original tier being moved up or down such that the end tier and the associated claim adjudication instructions used by the POS 100 may provide a benefit or a detriment to the member, for example by raising or lowering the copay amount.

Advantageously, benefits module 110 is also configured to provide claim adjudication instructions to the POS module 100 that will allow a member to purchase a particular drug at the same copay level as a prior purchase of the same drug by the member within a particular time frame, even if the drug is no longer covered by the prescription drug benefits program. Accordingly, if a claim for such a prior purchase is stored in the claim history for the particular member, the benefits module 110 provides claim adjudication instructions to the PBM module 100 that result in an approved claim adjudication for the current claim adjudication request. For example, if the prescribed drug is no longer part of the formulary for the program but the member had previously purchased the prescribed drug and then later attempted to purchase a refill within an approved time period, the benefits module 110 provides to the POS module 100 instructions that will result in an approved claim adjudication by the POS module 100. These unique capabilities of the benefits module 110 to potentially motivate and/or deter member behavior through economic means and approve a prescription drug purchase that would be disallowed under the current prescription drug benefits program because the prescription drug purchase for that member was previously allowed provide significant new flexibility and functionality to prescription drug benefit program administrators.

Figure 3:
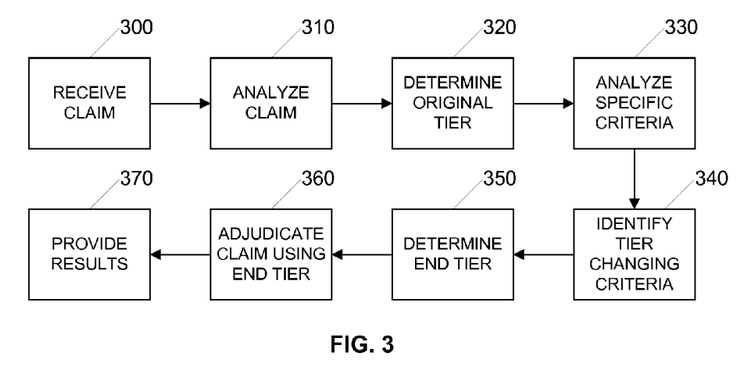
FIG. 3 is a flow diagram illustrating an example process for dynamic claims adjudication according to an embodiment of the invention.

FIG. 3 is a flow diagram illustrating an example process for dynamic claims adjudication according to an embodiment of the invention. In one embodiment, the illustrated process can be implemented by the processor enabled PBM 30 previously described with respect to FIGS. 1 and 2. It should be understood that the various steps in the process may be performed in an alternate order or in combination with other steps that are not shown. Initially, in step 300, the PBM receives a claim adjudication request. The claim adjudication request may include information regarding a prescription drug benefits program, a member of the prescription drug benefits program, and a drug that the member is attempting to purchase, among other information. For example, the member may be attempting to fill a prescription at a brick and mortar or online pharmacy such that the claim adjudication request is received from the pharmacy by the PBM via a data communication network.

Upon receipt of the claim adjudication request, the PBM analyzes the claim in step 310. The claim analysis may parse the claim to identify the program, the drug, the member and other information that facilitates efficient and quick adjudication of the claim adjudication request. Additional information may be obtained by the PBM from data storage in order to more accurately adjudicate the claim. In step 320, the PBM determines the original tier for adjudicating the claim adjudication request. In one embodiment, the original tier is determined by an analysis of the formulary, which identifies the universe of drugs available under the program and groups the drugs together into tiers based on criteria established by or for the program.

In step 330, the PBM next analyzes specific criteria. The specific criteria can be related to the particular member, the particular drug, or the particular program that is associated with the claim adjudication request. In one embodiment, member-specific criteria may include historical claim adjudication information. For example, sequential purchase of a generic drug and a second drug according to a particular timeline can be helpful member specific historical claim adjudication information because it may confirm that the member has followed a particular set of steps that are desirable. In such a case, confirmation that the member has followed the desired step-therapy results in the PBM identifying a tier changing criteria, as shown in step 340.

When the PBM identifies one or more tier changing criteria, in step 350 the PBM analyzes the one or more tier changing criteria to determine an end tier. The end tier is what the PBM will use to adjudicate the claim adjudication request. Next, in step 360, the PBM adjudicates the claim. Claim adjudication may include dynamically obtaining claim adjudication instructions based on information related to the particular claim being adjudicated. For example, claims being adjudicated with respect to different tiers use different sets of tier specific instructions for adjudication.

Advantageously, the analysis of specific information and the corresponding identification of tier changing criteria allow the PBM to flexibly implement the policies set forth in the prescription drug benefit program during dynamic claim adjudication. Accordingly, program members who follow certain step therapies are dynamically rewarded when purchasing prescriptions, for example by lower copays. These rewards in turn facilitate future compliance with the policies set forth in the prescription drug benefit program to the benefit of the members, the program, and the overall health care system because adherence to the designed step therapies can improve member health care are reduce overall costs. Finally, after the claim has been adjudicated in step 360, the results are provided in step 370 in response to the claim adjudication request.

Figure 4:
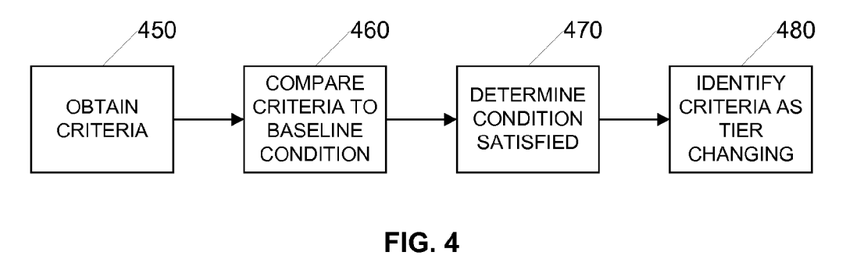
FIG. 4 is a flow diagram illustrating an example process for identifying tier changing criteria according to an embodiment of the present invention.

FIG. 4 is a flow diagram illustrating an example process for identifying tier changing criteria according to an embodiment of the present invention. In one embodiment, the illustrated process may be carried out by the processor enabled PBM 30 previously described with respect to FIGS. 1 and 2. It should be understood that the various steps in the process may be performed in an alternate order or in combination with other steps that are not shown. Initially, in step 450, the PBM obtains data regarding one or more criteria that are to be analyzed as potential tier changing criteria. The criteria may be a single criterion, for example, the existence of a prior purchase of a particular drug in the claim history for the member. Additionally, the criteria may include a plurality of related criteria that collectively may result in the identification of a tier changing criteria.

Next, in step 460 the PBM compares the one or more criteria to a baseline condition. The baseline may be a simple Boolean trigger such as the existence of a prior claim in the member's claim history as previously described. Additionally, the baseline may be an aggregate of particular items in a desired step therapy. In one embodiment, when comparing the criteria to the baseline, the PBM may access information in data storage area 35 and engage a plurality of modules that also access information in data storage area 35 in order to compare the one or more criteria to all aspects of the baseline. After the comparison of the one or more criteria to the baseline has been made, the PBM determines in step 470 if the one or more criteria satisfy the baseline condition. If the one or more criteria do satisfy the baseline condition, then the one or more criteria are identified as a tier changing criteria, as shown in step 480.

Figure 5:
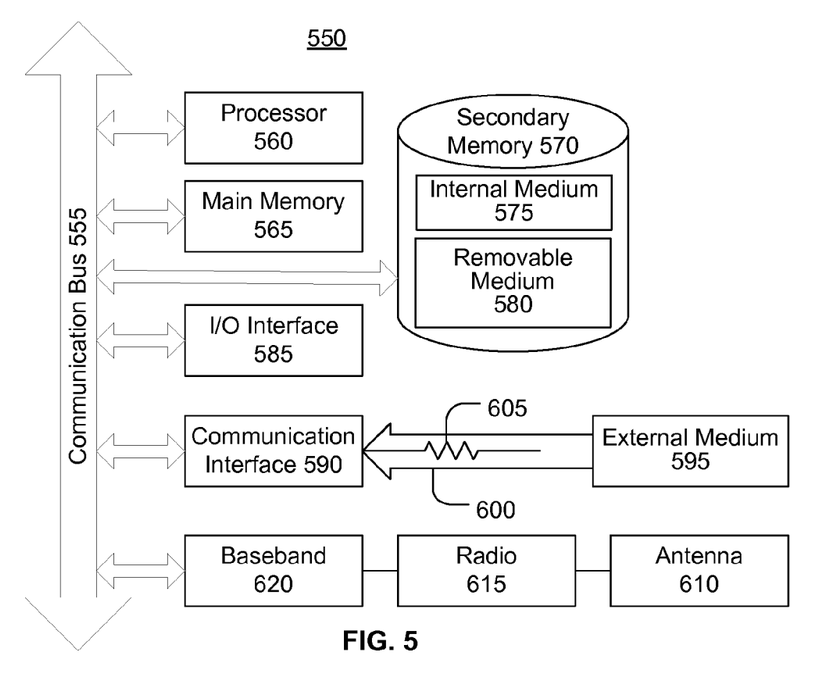
FIG. 5 is a block diagram illustrating an example computer system that may be used in connection with various embodiments described herein.

FIG. 5 is a block diagram illustrating an example computer system 550 that may be used in connection with various embodiments described herein. For example, referring to FIG. 1, the computer system 550 may be used as or in conjunction with a device at the pharmacy 20 or the PBM 30 to facilitate wired or wireless communication over network 40. The computer system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The computer system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the computer system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the computer system 550 for execution by the processor 560.

In alternative embodiments, secondary memory 570 may include other similar means for allowing computer programs or other data or instructions to be loaded into the computer system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the computer system 550.

Computer system 550 may also include a communication interface 590. The communication interface 590 allows software and data to be transferred between computer system 550 and external devices (e.g. printers), networks, or information sources. For example, computer software or executable code may be transferred to computer system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication link. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the computer system 550 to perform the various functions of the present invention as previously described.

In this description, the term "computer readable medium" is used to refer to any non-transitory computer readable storage media used to provide computer executable code (e.g., software and computer programs) to the computer system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the computer system 550.

In an embodiment that is implemented using software, the software may be stored on a computer readable medium and loaded into computer system 550 by way of removable medium 580, I/O interface 585, or communication interface 590. In such an embodiment, the software is loaded into the computer system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 620, a radio system 615 and a baseband system 610. In the communication device 550, radio frequency ("RF") signals are transmitted and received over the air by the antenna system 620 under the management of the radio system 615.

In one embodiment, the antenna system 610 may comprise one or more antennae and one or more multiplexors (not shown) that perform a switching function to provide the antenna system 620 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 610.

If the received signal contains audio information, then baseband system 610 decodes the signal and converts it to an analog signal. Then the signal is amplified and sent to a speaker. The baseband system 610 also receives analog audio signals from a microphone. These analog audio signals are converted to digital signals and encoded by the baseband system 610. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 620 where the signal is switched to the antenna port for transmission.

The baseband system 610 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the communication device 550 to perform the various functions of the present invention as previously described. For example, data storage areas 565 may include various software modules (not shown) that were previously described with respect to FIGS. 2 and 3.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A system for dynamic claim adjudication, the system comprising:
   a non-transitory computer readable medium configured to store computer executable programmed modules and information;
   a processor communicatively coupled with the non-transitory computer readable medium configured to obtain information and execute programmed modules stored therein;
   a members module stored in the non-transitory computer readable medium and configured to be executed by the processor to store in the medium information about a plurality of members of one or more prescription drug benefits programs;
   a drugs module stored in the non-transitory computer readable medium and configured to be executed by the processor to store in the medium information about a plurality of drugs;
   a claims module stored in the non-transitory computer readable medium and configured to be executed by the processor to store in the medium information about a plurality of previously adjudicated claims;
   a benefits module stored in the non-transitory computer readable medium and configured to be executed by the processor to implement a prescription drug benefits program; and
   a point of sale module stored in the non-transitory computer readable medium and configured to be executed by the processor to
   receive a claim adjudication request for a prescription drug benefits program, wherein the claim adjudication request comprises an identification of a member and an identification of a drug,
   obtain information relating to the claim adjudication request from one or more of the members module, the drugs module, the claims module, and the benefits module,
   if the drug is included in a formulary of the prescription drug benefits program,
      analyze said information to determine an original tier for the claim adjudication request,
      determine whether one or more tier changing criteria apply to the claim adjudication request,
      if it is determined that one or more tier changing criteria apply, determine an end tier based on said one or more tier changing criteria, obtain claim adjudication instructions associated with said end tier, and implement those claim adjudication instructions to adjudicate the claim adjudication request in accordance with said end tier, and,
      if it is determined that no tier changing criteria apply, obtain claim adjudication instructions associated with said original tier, and implement those claim adjudication instructions to adjudicate the claim adjudication request in accordance with said original tier, if the drug is not included in the formulary of the prescription drug benefits program, determine whether the drug was previously purchased by the member, within a predetermined time period, based on one or more previously adjudicated claims for the member stored in the medium, and, if it is determined that the drug was previously purchased by the member within the predetermined time period, adjudicate the claim adjudication request by approving the drug even though it is not included in the formulary of the prescription drug benefits program, and provide results of said adjudication in response to the claim adjudication request.

2. The system of claim 1, further comprising an administrative module stored in the non-transitory computer readable medium and configured to be executed by the processor to manage the functionality of the benefits module.

3. The system of claim 1, further comprising a reporting module stored in the non-transitory computer readable medium and configured to be executed by the processor to provide information including the original tier and the end tier for one or more adjudicated claims.

4. The system of claim 3, wherein the reporting module is further configured to provide information including a reason why the original tier was changed to the end tier for one or more adjudicated claims.

5. The system of claim 1, wherein the claim adjudication request further comprises an identification of the prescription drug benefits program, and wherein the members module is further configured to validate that the member associated with the claim adjudication request is covered by said prescription drug benefits program.

6. The system of claim 5, wherein the benefits module is further configured to validate the inclusion of the drug in the formulary.

7. The system of claim 6, wherein the benefits module is further configured to identify the original tier based on the formulary.

8. The system of claim 1, wherein the members module is further configured to provide the point of sale module with one or more potential tier changing criteria.

9. A computer implemented method for dynamic claim adjudication, where one or more processors are programmed to perform steps comprising:

receiving a claim adjudication request identifying a prescription drug benefits program, a member of said program, and a drug to be purchased;

obtaining from a data storage area information related to the program, the member, and the drug;

determining whether the drug is included in a formulary of the prescription drug benefits program;

if it is determined that the drug is included in the formulary, analyzing the claim adjudication request and the information from the data storage area to determine an original tier, analyzing the claim adjudication request and the information from the data storage area to determine whether one or more tier changing criteria apply to the claim, if it is determined that one or more tier changing criteria apply, determining an end tier based on said one or more tier changing criteria, and adjudicating the claim in accordance with said end tier, and, if it is determined that no tier changing criteria apply, adjudicating the claim in accordance with said original tier;

if it is determined that the drug is not included in the formulary, determining whether the drug was previously purchased by the member, within a predetermined period of time, based on one or more previously adjudicated claims for the member stored in the data storage area, and, if it is determined that the drug was previously purchased by the member within the predetermined period of time, adjudicating the claim by approving the drug even though it is not included in the formulary of the prescription drug benefits program; and providing results of said claim adjudication in response to receiving the claim adjudication request.

10. The method of claim 9, further comprising:
obtaining prescription drug benefits program specific information from a data storage area; and
using the prescription drug benefits program specific information to validate that the member is covered by the prescription drug benefits program.

11. The method of claim 9, further comprising:
obtaining formulary specific information from a data storage area; and
using the formulary specific information to validate the inclusion of the drug in the formulary, wherein said formulary identifies the original tier for adjudicating the claim.

12. The method of claim 9, further comprising analyzing the member information retrieved from the data storage area to identify the tier changing criteria.

13. The method of claim 9, further comprising analyzing prior authorization information to determine that the claim adjudication request has no associated prior authorization edits.

14. The method of claim 9, further comprising:
obtaining instructions associated with the end tier; and
executing said instruction to adjudicate the claim adjudication request.

15. A non-transitory computer readable medium having stored thereon one or more sequences of instructions for causing one or more processors to perform the steps for dynamic claim adjudication, the steps comprising:

receiving a claim adjudication request identifying a prescription drug benefits program, a member of said prescription drug benefits program, and a drug to be purchased;

obtaining from a data storage area information related to the prescription drug benefits program, the member, and the drug;

determining whether the drug is included in a formulary of the prescription drug benefits program;

if it is determined that the drug is included in the formulary, analyzing the claim adjudication request and the information from the data storage area to determine an original tier, analyzing the claim adjudication request and the information from the data storage area to determine whether one or more tier changing criteria apply to the claim, if it is determined that one or more tier changing criteria apply, determining an end tier based on said one or more tier changing criteria, and adjudicating the claim in accordance with said end tier, and,
if it is determined that no tier changing criteria apply, adjudicating the claim in accordance with said original tier;
if it is determined that the drug is not included in the formulary,
determining whether the drug was previously purchased by the member, within a predetermined time period, based on one or more previously adjudicated claims for the member stored in the data storage area, and,
if it is determined that the drug was previously purchased by the member within the predetermined time period, adjudicating the claim by approving the drug even though it is not included in the formulary of the prescription drug benefits program; and
providing results of said claim adjudication in response to receiving the claim adjudication request.

16. The medium of claim 15, wherein the steps further comprise:
obtaining prescription drug benefits program specific information from a data storage area; and
using the prescription drug benefits program specific information to validate that the member is covered by the prescription drug benefits program.

17. The medium of claim 15, wherein the steps further comprise:
obtaining formulary specific information from a data storage area; and
using the formulary specific information to validate the inclusion of the drug in the formulary, wherein said formulary identifies the original tier for adjudicating the claim.

18. The medium of claim 15, further comprising analyzing the member information retrieved from the data storage area to identify the tier changing criteria.

19. The medium of claim 15, further comprising analyzing prior authorization information to determine that the claim adjudication request has no associated prior authorization edits.

20. The medium of claim 15, further comprising:
obtaining instructions associated with the end tier; and
executing said instruction to adjudicate the claim adjudication request.

* * * * *